United States Patent [19]

Buckle et al.

[11] 4,378,360
[45] Mar. 29, 1983

[54] 6-{3-[4-(SUBSTITUTED BENZYL)-1-PIPERAZINYL]PROPYLOXY}-4,9-DIHYDRO-4,9-DIOXO-1H-NAPHTHO[2,3-D-]-V-TRIAZOLE

[75] Inventors: Derek R. Buckle, Redhill; Harry Smith, Maplehurst, Near Horsham; John M. Tedder, Redhill, all of England

[73] Assignee: Beecham Group Limited, England

[21] Appl. No.: 254,372

[22] Filed: Apr. 15, 1981

[30] Foreign Application Priority Data

Apr. 22, 1980 [GB] United Kingdom ................ 8013267

[51] Int. Cl.³ ................ C07D 246/16; A61K 31/495; C07D 295/02
[52] U.S. Cl. .................................... 424/250; 544/366; 548/259
[58] Field of Search .................... 544/366; 424/250

[56] References Cited

U.S. PATENT DOCUMENTS 4,263,299 4/1981 Buckle et al. .............. 544/250
4,263,309 4/1981 Buckle et al. .............. 544/250

OTHER PUBLICATIONS

McOmie, J. F., "Protective Groups in Organic Chemistry", pp. 197–199, (1973).

Primary Examiner—Donald G. Daus
Assistant Examiner—Sharon A. Gibson
Attorney, Agent, or Firm—Jacobs & Jacobs

[57] ABSTRACT

Compounds of formula (I):

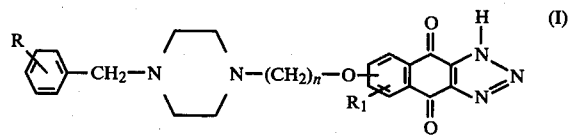

wherein R is hydrogen, halogen, $C_{1-4}$ alkyl or $C_{1-4}$ alkoxy; $R_1$ is hydrogen or $C_{1-6}$ alkyl; and n is 1 to 6 and pharmaceutically acceptable salts thereof; pharmaceutical compositions containing them; a process for their preparation; and their use in treating allergy.

15 Claims, No Drawings

6-{3-[4-(SUBSTITUTED BENZYL)-1-PIPERAZINYL]PROPYLOXY}-4,9-DIHYDRO-4,9-DIOXO-1H-NAPHTHO[2,3-d-]-v TRIAZOLE

This invention relates to novel compounds, pharmaceutical compositions containing them, their formulation into pharmaceutical compositions, their use in therapy, and a process for their preparation.

It is known that some types of cells are activated by certain antibody-antigen combinations and release substances which mediate the allergic response. British Pat. No. 1 454 247 discloses that certain substituted 3-nitrocoumarins have useful activity in that they appear to inhibit the release of substances such as histamine which are normally released after antibody-antigen combinations and which mediate the allergic response.

European Patent Application No. 78300485.6 (also allowed U.S. patent application Ser. No. 953,464 filed Oct. 23, 1978) discloses a class of compounds of the formula (A), their preparation, and that they also have this type of activity:

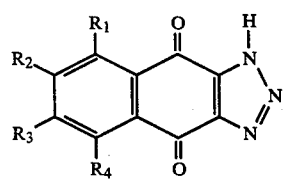
(A)

wherein $R_1$, $R_2$, $R_3$ and $R_4$ represent hydrogen, halogen, nitro, lower alkyl or lower alkoxy, or any adjacent two of $R_1$ to $R_4$ taken together represent an alkylene group containing from 3 to 5 carbon toms or a 1,4-buta-1,3-dienylene group, and pharmaceutically acceptable salts thereof.

We have now discovered a class of compounds which not only inhibit the release of mediator substances but also antagonise the effects of histamine released after the above-mentioned antibody-antigen combinations. Thus these compounds are of value in the prophyaxis and treatment of diseases whose symptoms are controlled by the mediators of the allergic response, for example asthma, hay-fever, rhinitis and allergic eczema.

Accordingly the present invention provides a compound of the formula (I), a pharmaceutically acceptable salts thereof:

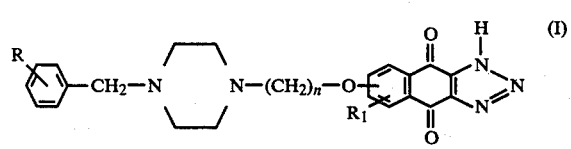
(I)

wherein R is hydrogen, halogen, $C_{1-4}$ alkyl or $C_{1-4}$ alkoxy; $R_1$ is hydrogen or $C_{1-6}$ alkyl; and n is 1 to 6.

Suitable examples of R include hydrogen; chlorine, bromine; methyl, ethyl; methoxy and ethoxy. More suitably R is hydrogen or halogen, preferably chlorine. Most suitably R is 2, 3 or 4-chloro, for example 4-chloro.

Suitable examples of $R_1$ include hydrogen, methyl, ethyl and n- and iso-propyl. When other than hydrogen, $R_1$ is suitably in the 5-position in the 4,9-dihydro-4,9-dioxo-1H-naphtho[2,3-d]-v-triazole nucleus (that is, substituting either carbon atom adjacent to the bridgehead carbon atoms, these bridgehead atoms being tautomerically equivalent). Preferably $R_1$ is hydrogen or 5-methyl.

n is suitably 2, 3 or 4, preferably 3.

The side chain oxygen atom may join the naphthoquinone moiety at any non-bridgehead carbon in the benzene ring, such as the 5- or 6-position. Often it will be joined at the 6-position (that is, substituting either carbon atom meta- to either bridgehead carbon atom. It will be appreciated that, when $R_1$ is $C_{1-6}$ alkyl in the 5-position, the 6-position will be defined thereby.

From the aforesaid it will be appreciated that one preferred sub-group of compounds of the formula (I) is of formula (II):

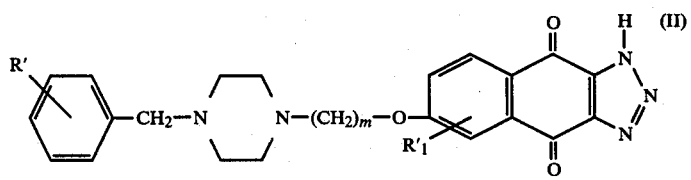
(II)

wherein R' is hydrogen or halogen, $R_1'$ is hydrogen or $C_{1-6}$ alkyl, and m is 2, 3 or 4.

Suitable and preferred values for R', $R_1'$ and m are as hereinbefore described for R, $R_1$ and n respectively.

Thus R' when halogen, is suitably in the 2, 3 or 4-position, and preferably is chloro, for example 4-chloro.

Similarly $R_1'$ when alkyl is preferably in the 5-position, for example 5-methyl.

The triazole moiety of the compounds of formula (I) has an acidic hydrogen, and accordingly may form salts. Examples of pharmaceutically acceptable salts falling within the scope of this invention include the aluminium, alkali metal and alkaline earth metal salts such as the sodium, potassium and magnesium salts; and salts with ammonia, organic bases and amino compounds.

The present invention also provides a process for the preparation of a compound of the formula (I), which process comprises the reaction of a compound of the formula (III):

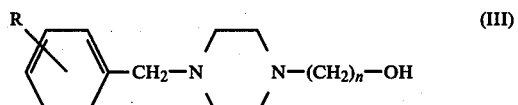
(III)

wherein the variables are as defined in formula (I), with a compound of the formula (IV):

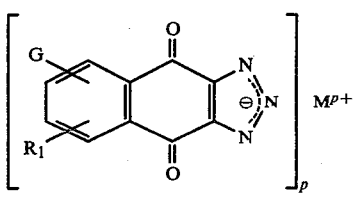

(IV)

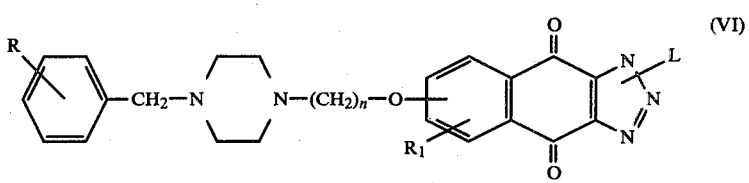

wherein p is 1 or 2; $M^{p+}$ is a p-valent cation; G is a group readily displaceable by a nucleophile from an aromatic nucleus; and $R_1$ is as defined in formula (I).

Suitable examples of G include halogen atoms such as fluorine, chlorine, bromine or iodine; or nitro.

The reaction is generally carried out in the presence of a strong base in a polar solvent, some of the polar solvent often going to form the base. Examples of suitable bases include sodium in an alcohol such as tert-butanol, sodium hydride or hydroxide in dimethylsulphoxide or dimethylformamide and lithium di-isopropylamide in hexamethylphosphoramide.

The cation $M^{p+}$ in the compound of the formula (IV) may suitably be any of the mono- or divalent metal salifying cations described hereinbefore in examples of salts of the compounds of formula (I). When the reaction is carried out in the presence of a strong base in a polar solvent it is often convenient for the compound of the formula (IV) and the base to have a common cation, for example sodium.

Temperatures of 5° to 90° C. may be used depending on the solvent, base and particular starting materials employed. The reaction time will depend on these parameters and on the temperature employed, and this may readily be determined by routine trial and error. The reaction may be monitored by conventional methods such as thin layer chromatography. By way of example a reaction time of up to 1 hour is often suitable at ambient temperatures.

The compounds of formula (III) are either known compounds or may be prepared in analogous manner to known compounds.

The compounds of formula (IV) may be prepared from the corresponding compounds of formula (V):

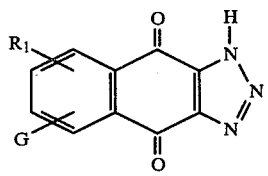

(V)

wherein $R_1$ and G are as defined in formula (IV) by neutralisation with a suitable base in a solvent compatible with the base. Thus, when $M^{p+}$ is a monovalent cation, for example an alkali metal cation, neutralisation may conveniently be effected using the corresponding hydroxide in water. The reaction may be monitored by means of a pH meter, adjusting the pH to 7.0. When $M^{p+}$ is magnesium an equivalent of magnesium ethoxide in ethanol may be used.

The present invention also provides a second process for the preparation of a compound of the formula (I), which process comprises the de-protection of a compound of the formula (VI):

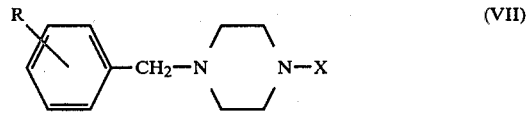

(VI)

wherein L is a protecting group and the remaining variables are as defined in formula (I).

As novel intermediates, compounds of formula (VI) form an important aspect of this invention.

L may suitably be a N-protecting group removable by acidolysis with a strong acid. Suitable examples of L include labile benzyl groups or trityl. Examples of labile benzyl groups include benzyl substituted in the phenyl ring by one or more $C_{1-4}$ alkoxy groups, such as 4-methoxy,2,4-dimethoxy or 2,4,6-trimethoxy-benzyl. Two particularly suitable examples of L are 4-methoxybenzyl and trityl.

L may be present on any one of the three positions in the triazole nucleus.

L may be removed in any convenient way which does not disrupt any other part of the molecule, such as by acidolysis. Strong acids such as trifluoroacetic or methanesulphonic acids are suitable. The reaction may of course be monitored by n.m.r. spectroscopy, but we have found that a temperature of 40° to 85° C., for example 50° to 70° C. and a reaction time of 6 to 8 hours are appropriate.

The compounds of the formula (VI) may themselves be prepared by coupling a compound of the formula (VII) with a compound of the formula (VIII):

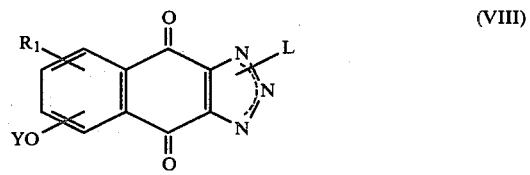

(VII)

(VIII)

wherein X is hydrogen and Y is a group $Z(CH_2)_n$ where Z is a group readily displaceable from an aliphatic moiety by a nucleophile; or X is a group $(CH_2)_nOH$ and Y is hydrogen; and n is as defined in formula (I).

The reaction conditions vary with the values of X and Y:

(i) X is hydrogen and Y is a group $Z(CH_2)_n$ in compounds (VII) and (VIII)

Suitable examples of Z include halogen atoms such as chlorine, bromine and iodine, and activated ester groups such as methanesulphonate and tosylate groups.

The reaction is generally carried out in the presence of a moderate base in a polar solvent. Examples of suitable bases include basic alkali metal salts such as the carbonates, for instance potassium carbonate. Examples of suitable solvents include ketones; such as methyl ethyl ketone.

The reaction is conveniently carried out under reflux at temperatures of 50° to 110° C. depending on the solvent, base and particular starting materials employed. The reaction time will depend on these parameters and on the temperature employed and this may readily be determined by routine trial and error. The reaction may be monitored by conventional methods such as thin layer chromatography. By way of example a reaction time of up to 6 hours is often suitable.

Compounds of formula (VII) in this case are either known compounds or may be prepared analogously to known compounds.

Compounds of the formula (VIII) wherein Y is $Z(CH_2)_n$ as hereinbefore defined may be prepared by the reaction of a corresponding compound of the formula (VIII) wherein Y is H, with a compound of the formula (IX):

  A(CH₂)ₙB  (IX)

wherein A is Z as hereinbefore defined or hydroxyl and B is chlorine, bromine or iodine, and, when A is hydroxyl, subsequently esterifying A to give an activated ester group.

The reaction is generally carried out in the presence of a moderate base in a polar solvent. Examples of suitable bases include basic alkali metal salts such as the carbonates, for instance potassium carbonate. Examples of suitable solvents include ketones; such as methyl ethyl ketone.

Compounds of the formula (VIII) wherein Y is H may be prepared by reaction of a compound of formula (X):

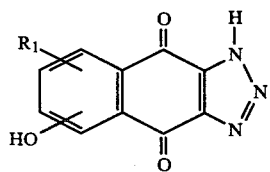

(X)

with a compound of formula LB wherein L and B are as hereinbefore defined.

(ii) X is $(CH_2)_nOH$, Y is H in the compounds (VII) and (VIII)

The reaction of these compounds of formula (VII) and (VIII) is generally carried out in the presence of a compound of formula (XI):

  $R_3O_2C-N=N-CO_2R_4$  (XI)

wherein $R_3$ and $R_4$ are independently $C_{1-6}$ alkyl, aryl or aryl-$C_{1-6}$ alkyl, generally both ethyl, and a compound of formula (XII).

  $PR_5R_6R_7$  (XII)

wherein $R_5$, $R_6$ and $R_7$ are independently $C_{1-6}$ alkyl, $C_{1-6}$ alkoxy, aryl, aryloxy, aryl-$C_{1-6}$ alkyl or aryl-$C_{1-6}$ alkoxy, generally all phenyl.

The reaction is generally carried out at a non-extreme temperature, such as −20° to 100° C., in an inert aprotic organic solvent such as tetrahydrofuran, dioxan, ethyl acetate or benzene.

It will be realised that compounds of formula (VII) wherein X is $(CH_2)_nOH$ are of formula (III), discussed hereinbefore.

The preparation of compounds of formula (VIII) wherein Y is H from compounds of formula (X) has been discussed hereinbefore.

It is believed that the preparation of compounds of the formula (VI) by means of this process involving compounds of the formula (VII) and (VIII) wherein X is $(CH_2)_nOH$ and Y is H, and compounds of the formula (XI) and (XII), is a preferred process of this invention.

In the preparation of a compound of formula (VIII) wherein Y is H, hereinafter referred to as a compound of formula (VIII)', from a compound of formula (X):

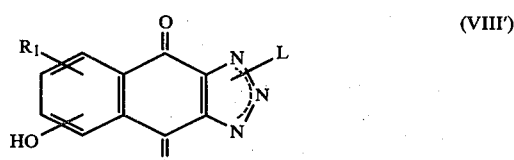

(VIII')

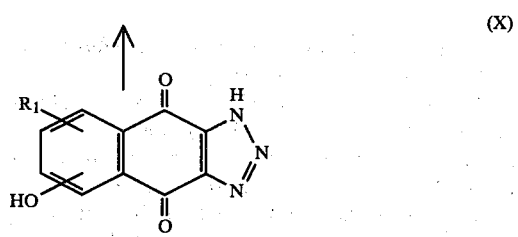

(X)

the N-protection with the L group results in each of the three possible isomers being formed when L is 4-methoxybenzyl. For a given configuration of the $R_1$ and OH substituents, each of these three possible isomers may be separated if desired by the usual methods.

PREPARATION OF INTERMEDIATE COMPOUNDS OF FORMULAE (V) AND (X)

Section A

Compounds of formulae (V) and (X) may be represented by general formula (XIII):

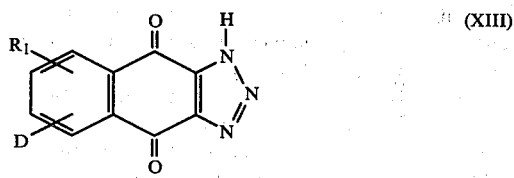

(XIII)

wherein D is hydroxyl or G as in formula (IV) and $R_1$ is as defined in formula (I).

The compounds of formula (XIII) may be prepared by the methods disclosed in European Patent Application No. 78 300485.6. It will be appreciated that any particular method will be chosen having regard to its compatibility with the group D.

The first such method comprises oxidizing a naphthotriazole of formula (XIV):

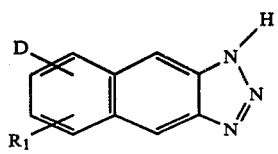

(XIV)

wherein $R_1$ and D are as defined with reference to formula (XIII) with a powerful oxidizing agent.

Suitable oxidizing agents include chromium trioxide and chromic acid. The method is carried out in a manner analogous to that described by K. Fries, R. Walter and K. Schilling, *Annalen* 576, 248, (1935), for the preparation of 4,9-dihydro-4,9-dioxo-1H-naptho[2,3d]-v-triazole.

A second method comprises deamination of a 2-amino-naphtho-v-triazole (XV):

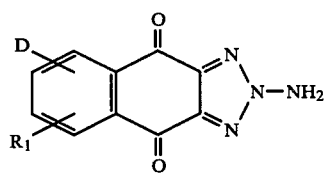

(XV)

wherein $R_1$ and D are as defined with reference to formula (XIII) above, with nitrous acid.

The method is carried out in a manner analogous to that described by W. L. Mosby and M. L. Silva, *J. Chem. Soc.*, 1003 (1965), for the preparation of 4,9-dihydro-4,9-dioxo-1H-naphtho[2,3-d]-triazole.

However, we have found that compounds of formula (XIII) above are most conveniently made by a process which comprises reacting a compound of formula (XVI):

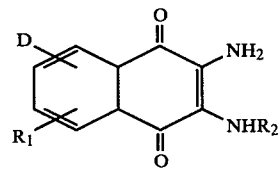

(XVI)

wherein $R_1$ and D are as defined with reference to formula (XIII) and $R_2$ is hydrogen or an acyl group, with nitrous acid.

Suitable acyl groups include benzoyl and lower alkanoyl, Examples of suitable lower alkanoyl groups are acetyl, propionyl and butyryl.

The nitrous acid is most suitably generated in situ from an alkali metal nitrite and an acid.

Most suitably the alkali metal nitrite is sodium nitrite, and the acid is a mineral acid such as hydrochloric acid.

The reaction is carried out in a solvent which is inert to the reagents and products. Examples of such solvents include water and acetic acid.

We have found water to be most convenient.

The reaction should be carried out at room temperature or below i.e. preferably between 0° C. and 25° C.

The preparation of the compounds of formula (XIII) from the quinone intermediates (XVI) is facilitated by reducing the quinone to the corresponding hydroquinone, (XVII):

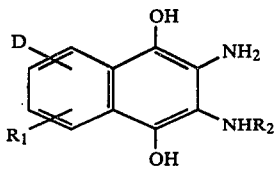

(XVII)

wherein $R_1$, $R_2$ and D are as defined with reference to formula (XVI) above and reacting the hydroquinone (XVII) with nitrous acid. These are generally more soluble in acid media than the quinones. The reduction may be carried out using any standard method for reducing quinones to hydroquinones. We have found sodium dithionite to be a most convenient reducing agent for this purpose. The hydroquinones (XVII) oxidize to the parent quinone during the reaction with nitrous acid.

Section B

Compounds of the formula (X):

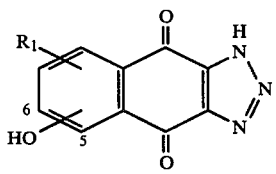

(X)

may alternatively be prepared in a number of ways, depending on the position of the HO— moiety.

(a) With the HO— moiety at position 6; and $R_1$ is H, a most suitable synthesis is by the photolysis of the parent naphthotriazole of formula (XVIII):

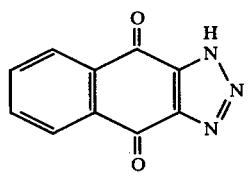

(XVIII)

in sulphuric acid. A reasonable conversion has been found to occur after about 80 hours.

(b) With the HO— moiety at position 5, and $R_1$ is H, a most suitable synthesis is by nitration of the parent naphthotriazole of formula (XVIII), followed by nucleophilic displacement of the nitro group.

This nitration, which may be carried out in known manner, for example as described in European Patent Application No. 78300485.6, gives a 9:1 ratio of the 5-nitro and 6-nitro compounds. From this mixture the desired 5-nitro compound is readily isolated by fractional crystalisation (the 6-nitro compound can also be isolated if desired, but only with difficulty).

The nucleophilic displacement of the 5-nitro group is conveniently carried out on the sodium salts of the nitro-triazole (to protect the triazole N—H) at room temperature in a solvent such as dimethyl sulphoxide, with aldoximate anion, the reaction time being less than twenty four hours. (If desired this displacement reaction can also of course be carried out on the 6-nitro triazole).

The parent naphthotriazole of formula (XVIII) can of course be prepared by methods as described in the said European Patent Application No. 78300485.6, as also described hereinbefore.

As previously stated, the compounds of formula (I) are active therapeutically.

Accordingly, this invention also provides a pharmaceutical composition comprising a compound of formula (I) as defined above, or a pharmaceutically acceptable salt thereof, and a pharmaceutically acceptable carrier.

Examples of suitable and preferred compounds for inclusion in such compositions are as previously discussed.

The compositions are of course adapted for administration to human beings.

Compounds of formula (I) which are active when given by the oral route, may be compounded in the form of syrups, tablets, capsules, pills and the like. Preferably, the compositions are in unit dosage form, or in a form in which the patient can administer to himself a single dosage. When the composition is in the form of a tablet, powder or lozenge, any pharmaceutical carrier suitable for formulating solid compositions may be used. Examples of such carriers are magnesium stearate, starch, lactose, glucose, sucrose, rice flour and chalk. The composition may also be in the form of an ingestible capsule (e.g. of gelatin) containing the compound; or in the form of a syrup, a liquid solution or a suspension. Suitable liquid pharmaceutical carriers include ethyl alcohol, glycerine, saline and water which may be compounded with flavouring or colouring agents to form syrups.

The compounds of this invention may also be administered by a non-oral route. In accordance with routine pharmaceutical procedure, the compositions may be formulated, for example for rectal administration as a suppository or for presentation in an injectable form in an aqueous or non-aqueous solution, suspension or emulsion in a pharmaceutically acceptable liquid, e.g. sterile pyrogen-free water or a parenterally acceptable oil or a mixture of liquids, which may contain bacteriostatic agents, antioxidants or other preservatives, buffers solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn, or a solid form or concentrate which can be used to prepare an injectable formulation.

Compositions of this invention may also suitably be presented for administration to the respiratory tract as a snuff or an aerosol or solution for a nebulizer, or as a microfine powder for insufflation, alone or in combination with an inert carrier such as lactose. In such a case the particles of active compound suitably have diameters of less than 50 microns, preferably less than 10 microns. Where appropriate, small amounts of other anti-asthmatics and bronchodilators for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

Compounds of general formula (I) may also be presented as an ointment, cream, lotion, gel, aerosol, or skin paint for topical application.

It is preferred that the compounds of this invention are administered by inhalation.

By way of example, in any of the preceding formulations a suitable dosage unit might contain 0.01 to 500 mgs of active ingredient, more suitably 1 to 500 mgs via the oral route, 0.01 to 100 mg (such as 0.01 to 1 mg) via inhalation. The effective dose of compound (I) depends on the particular compound employed, the condition of the patient and on the frequency and route of administration, but in general is in the range of from 0.001 mg/kg/day to 100 mg/kg inclusive of the patients's body weight.

As in common practice, the compositions will usually be accompanied by written or printed directions for use in the medical treatment concerned, in this case as an anti-allergic agent for the prophylaxis and treatment of for example, asthma, hay-fever, rhinitis or allergic eczema.

The following Examples illustrate the preparation of compounds of this invention.

The following Descriptions illustrate the preparation of intermediates to these compounds.

DESCRIPTION 1

4,9-Dihydro-4,9-dioxo-6-fluoro-1H-naphtho[2,3-d]-v-triazole

To a stirred suspension of 2-acetamido-3-amino-6(7)-fluoronaphtho-1,4-quinone (1.0 g, 0.004 mole) in water (150 ml) was added a solution of sodium dithionite (2.5 g) in water (10 ml) in one portion. After a further 1 hour the precipitated hydroquinone was filtered off and suspended in 2 N HCl (50 ml) at 5° C. A solution of sodium nitrite (1.5 g) in water (15 ml) was added over 30 mins. and the mixture stirred overnight. The precipitated triazole was filtered off and recrystallised from acetone/water to give 0.55 g [63%] of derivative of mp 233° (dec),$\nu_{max}$(mull) 1690, 1600 cm$^{-1}$; M+ 217.0296, $C_{10}H_4FN_3O_2$.

DESCRIPTION 2

Sodium salt of 4,9-Dihydro-4,9-dioxo-6-fluoro-1H-naphtho[2,3-d]-v-triazole

To a stirred suspension of 4,9-dihydro-4,9-dioxo-6-fluoro-1H-naphtho[2,3-d]-v-triazole in water was added dropwise a solution of sodium hydroxide in water until the pH of the resulting solution was 7.0 as indicated by a pH meter. The solution was evaporated and the residue dried in vacuo at 2 mm and 100° for two hours to yield the anhydrous sodium salt.

EXAMPLE 1

6-{3-[4-(4-Chlorobenzyl)-1-piperazinyl]propyloxy}-4,9-dihydro-4,9-dioxo-1H-naphtho[2,3-d]-v-triazole

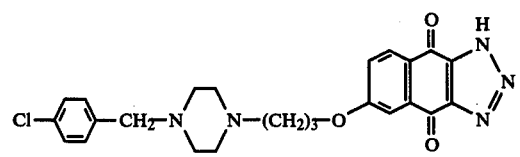

To a solution of sodium hydride (480 mg, 1 mmole of 50% dispersion) in dimethyl sulphoxide (10 ml) was added a solution of 3-[4-(4-chlorobenzyl)-1-piperazinyl]propanol (252 mg, 1 mmole) in dimethyl sulphoxide (2 ml) and the mixture stirred. To this was added a solution of 6-fluoro-4,9-dihydro-4,9-dioxo-1H-naphtho[2,3-d]-v-triazole sodium salt (240 mg, 1 mmole)

in dimethyl sulphoxide in one portion and the mixture stirred for 20 minutes and then filtered. Water (100 ml) was added and the resulting red solution was washed with ether and the pH adjusted to 4.8 with hydrochloric acid. The yellow solid which formed was filtered off and washed with hot acetone to give 85 mg (18%) of the title compound. $\nu_{max}$ (mull) 3250 (broad), 1675, 1599, 1250 cm$^{-1}$; (DMSO-d6) 2.1(2H, m); 2.7 (4H, m); 3.2 (6H, m); 3.65 (2H, s); 4.2 (2H, m); 7.4 (m) and 8.05 (d) (7H). mpt 234° C. dec.

DESCRIPTION 3

4,9-Dihydro-4,9-dioxo-6-hydroxy-1H-naphtho[2,3-d]-v-triazole 4,9-Dihydro-4,9-dioxo-1H-naphtho[2,3-d]-v-triazole monohydrate (1.8 g, 8.3 mmole) was dissolved in 98% sulphuric acid (700 ml) in a 1 liter photolysis unit equipped with a medium pressure lamp. Nitrogen was passed through the apparatus and the solution was photolysed for 40 hours. The solution was poured onto ice (3 kg) and extracted with ethyl acetate. The extracts were combined, dried and evaporated to yield a yellow solid (1.3 g). HPLC and NMR showed this to be a mixture of the starting material and the title compound in approximately equal proportions. Pure hydroxy compound could be obtained by recrystallisation of a sample from chloroform and had mp 216°–217° C. $\nu_{max}$(mull) ca 3400, 2800 (b), 1685, 1595, 1580, 1260 cm$^{-1}$.

δ[(CD$_3$)$_2$CO]: 7.30 (1H, dd, J=9.0 Hz, J$_2$2.0 Hz); 7.73 (1H, d, J=2.0 Hz); 8.17 (1H, d, J=9.0 Hz).

M+ (C$_{10}$H$_5$N$_3$O$_3$): 215.0312; Found: C, 53.57; H, 2.44; N, 18.88; C$_{10}$H$_5$N$_3$O$_3$.0.5H$_2$O. Requires: C, 53.58; H, 2.07; N, 18.75%.

[If desired this separation may be carried out *after* the protection reaction described in Description 4.]

DESCRIPTION 4

4,9-Dihydro-4,9-dioxo-6-hydroxy-N-(4-methoxybenzyl)-naphtho[2,3-d]-v-triazole 4,9-Dihydro-4,9-dioxo-6-hydroxy-1H-naphtho [2,3-d]-v-triazole (430 mg, 2.0 mmole) was treated with anhydrous potassium carbonate (152 mg, 1.1 mmole) in N,N-dimethylformamide (50 ml) and the mixture was stirred at 50° for 1 hour. 4-Methoxybenzyl chloride (500 mg, 3.2 mmole) was added and the mixture stirred at this temperature for a further 20 hours after which time the solvent was distilled in vacuo and the residue extracted with chloroform. Evaporation of the extracts gave 660 mg of a crude mixture of the three isomers of the title compound which were identified on the basis of their tlc properties. The fast running isomer being X, the second isomer being Y and the slowest running isomer being Z.

Chromatography on silica, gradient eluting with chloroform to chloroform ethanol (9:1) gave 180 mg of isomer X and 231 mg of a mixture of isomers Y and Z, giving a total yield of 411 mg (61.3%).

Isomer X: mp 267°–268° C., $\nu_{max}$(CHCl$_3$) 1695, 1660, 1652, 1630 cm$^{-1}$.

δ((CD$_3$)$_2$CO): 3.73 (3H, s, OCH$_3$); 5.77 (2H, s, CH$_2$); 7.15 (4H, AB quartet, J 9 Hz, Δν45 Hz, aromatics); 7.25 (1H, dd, J 4.5 Hz, J$_2$ 1.5 Hz, H-7); 7.57 (1H, d, J 1.5 Hz, H$_5$); 8.10 (1H, d, J 4.5 Hz, H$_8$).

M+ (C$_{18}$H$_{13}$N$_3$O$_4$): 335.0909. $\lambda_{max}$ (EtOH) 229 (10, 200), 249 (9,900) 397 (3,300) nm.

Isomer Y: not isolated pure.

Isomer Z: mp (isopropanol) 250° C., $\lambda_{max}$(mull) 1695, 1665, 1605, 1590, 1570, 1560, 1510 cm$^{-1}$.

δ (DMSO-d$_6$):3.73 (3H, s); 5.92 (2H, s); 7.14 (4H, AB quartet, J 9.1 Hz, Δν 32.5 Hz); 7.20 (1H, dd, J 2.5, 8.7 Hz); 7.47 (1H, d, J 2.5 Hz); 8.03 (1H, d, J 8.7 Hz); ca 11.0 (1H, broad, exchangeable).

DESCRIPTION 5

6{3-[4-(4-Chlorobenzyl)-1-piperazinyl]propyloxy}-4,9-dihydro-4,9-dioxo-N-(4-methoxybenzyl)naphtho[2,3-d]-v-triazole (i) 4,9-Dihydro-4,9-dioxo-6-hydroxy-N-(4-methoxybenzyl)naphtho[2,3-d]-v-triazole (pure isomer X, 180 mg, 0.53 mmole) was dissolved in dry tetrahydrofuran (15 ml) and 3-[4-(4-chlorobenzyl)-1-piperazinyl]-propanol (160 mg, 0.60 mmole) was added followed by triphenylphosphine (216 mg, 0.82 mmole). A solution of diethyl azodicarboxylate (195 mg, 1.12 mmole) in dry tetrahydrofuran (5 ml) was then added and the reaction monitored by HPLC. After 30 minutes the solvent was removed *in vacuo* and the residue chromatographed on silica eluting with chloroform to chloroform-10% methanol to give 114 mg of the title compound of mp (chloroform-acetone) 167°–169° C., $\nu_{max}$ (KBr) 3400 (br), 2940, 2805, 1690, 1685, 1610, 1590, 1250 cm$^{-1}$.

δ(CDCl$_3$): 2.00 (2H, m); 2.50 (10H, br s); 3.47 (2H, s); 3.80 (3H, s); 4.20 (2H, t); 5.73 (2H, s); 7.10 (4H, AB quartet, J=9 Hz, Δν=34 Hz); 7.27 (5H, m); 7.70 (1H, d, J=3 Hz); 8.23 (1H, d, J=9 Hz).

M+ (C$_{32}$H$_{32}$N$_5$O$_4$Cl): 585.2137.

Found: C, 65.36; H, 5.72; N, 12.10; C$_{32}$H$_{32}$N$_5$O$_4$Cl. Requires: C, 65.58; H, 5.50; N, 11.95%.

(ii) A similar reaction was carried out using a mixture of the three isomers X, Y and Z described above. Chromatography gave material identical to that obtained from isomer X above and a mixture of isomers derived from Y and Z which were not separated. This latter material was associated with half a mole of diethyl hydrazine dicarboxylate, possibly as a complex. δ(CDCl$_3$) methylene signals at 5.87 and 5.97 ppm.

EXAMPLE 2

6-{3-[4-(4-Chlorobenzyl)-1-piperazinyl]propyloxy}-4,9-dihydro-4,9-dioxo-1H-naphtho[2,3-d]-v-triazole

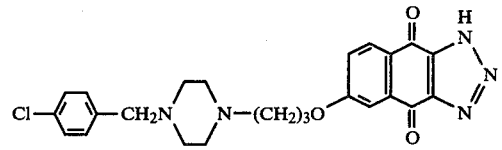

6-{3-[4-(4-Chlorobenzyl)-1-piperazinyl]propyloxy}-4,9-dihydro-4,9-dioxo-N-(4-methoxybenzyl(naphtho[2,3-d]-v-triazole (from isomer X, 501 mg, 0.853 mmole) was dissolved in trifluoroacetic acid (25 ml) at 60°. After 5 hours at this temperature the deprotection was complete by HPLC. The solvent was evaporated *in vacuo* and the residue taken up in dilute sodium hydroxide (0.1N, 50 ml), filtered, and washed with ethyl acetate. The aqueous phase was then adjsted to pH 4.8 with dilute hydrochloride acid and chilled when a yellow precipitate formed. This was collected and purified by chromatography on silica gel eluting with chloroform followed by increasing concentrations of methanol in chloroform until the product was eluted with 15% methanol in chloroform. Trituration of the product with acetone gave 197 mg (49.4%) of product as a pale yellow solid of mp 234° (dec), $v_{max}$ (mull) ca 2700 (br), 1680, 1595, 1250 cm$^{-1}$.

δ(DMSO-d$_6$): 2.10 (2H, m); 2.67 (4H, m); 3.17 (6H, m); 3.65 (2H, s); 4.13 (2H, t); 4.90 (ca 3H, br, exchanges); 7.07 (1H, dd, J$_1$=9 Hz, J$_2$=3 Hz); 7.30 (5H, m); 7.9 (1H, d, J=9 Hz).

Found: C, 61.01, H, 5.30; N, 15.01; C$_{24}$H$_{24}$N$_5$O$_3$Cl.½H$_2$O. Requires: C, 60.69; H, 5.31; N, 14.75%.

DESCRIPTION 6

6-{3-[4-(2-Chlorobenzyl)-1-piperazinyl]propyloxy}-4,9-dihydro-4,9-dioxo-N-(4-methoxybenzyl)naphtho[2,3-d]-v-triazole 4,9-Dihydro-4,9-dioxo-6-hydroxy-N-(4-methoxybenzyl)-naphtho[2,3-d]-v-triazole (mixed X, Y and Z isomers, 780 mg, 2.33 mmole) was dissolved in dry tetrahydrofuran (40 ml) and 3-[4-(2-chlorobenzyl)-1-piperazinyl]-1-propanol (689 mg, 2.57 mmole) was added followed by triphenylphosphine (936 mg, 3.57 mmole). A solution of diethyl azodicarboxylate (842 mg, 484 mmole) in dry tetrahydrofuran (20 ml) was then added and the reaction monitored by HPLC. After 30 minutes the solvent was removed *in vacuo* and the residue chromatographed on silica eluting with chloroform to yield a sample of an essentially single isomer [δ(CDCl$_3$) 5.70 (N—CH$_2$)] and a mixture of isomers [410 mg, 66.1%, δ(CDCl$_3$) 5.90 (N—CH$_2$)] of the title compound. The former contained diethyl hydrazinedicarboxylate possibly as a complex.

The pure isomer had: mp (acetone) 149°-150° C. $v_{max}$ (mull) 1695, 1685, 1605, 1595, 1505 cm$^{-1}$.

δ(CDCl$_3$): 2.01 (2H, quintet, J 5.3 Hz); 2.54 (10H, m); 3.63 (2H, s); 3.76 (3H, s); 4.20 (2H, t, J 5.3 Hz); 5.71 (2H, s); 7.33 (4H, AB quartet, J 8 Hz, Δν49 Hz); 7.63 (5H, m); 7.72 (1H, d, J 2.3 Hz).

M$^+$ (C$_{32}$H$_{32}$N$_5$O$_4$Cl) 585.2147.

EXAMPLE 3

6-{3-[4-(2-Chlorobenzyl)-1-piperazinyl]propyloxy}-4,9-dihydro-4,9-dioxo-1H-naphtho[2,3-d]-v-triazole

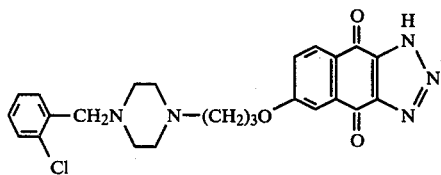

6{3-[4-(2-Chlorobenzyl)-1-piperazinyl]propyloxy}-4,9-dihydro-4,9-dioxo-N-(4-methoxybenzyl)naptho[2,3-d]-v-triazole (mixed isomers, 410 mg, 0.70 mmole) was dissolved in trifluoroacetic acid (20 ml) at 70°. After 4 hours at this temperature the deprotection was complete by HPLC. The solvent was evaporated and the residue was taken up in dilute sodium hydroxide (0.1N, 50 ml), filtered and washed with ethyl acetate (20 ml). The aqueous phase was then adjusted to pH 4.8 with dilute hydrochloric acid and chilled when a yellow precipitate formed. This was collected and purified by chromatography on silica eluting with chloroform grading to 15% methanol in chloroform to give a non crystalline foam which had an indistinct melting point. $v_{max}$ (mull) 1680, 1595, 1500 cm$^{-1}$.

δ(DMSO): 2.15 (2H, m); 2.74 (4H, m); 3.20 (6H, m); 3.68 (2H, s); 4.20 (2H, t, J=6 Hz); 4.60 (3H, brs, exchangeable); 7.13 (1H, dd, J$_1$=8 Hz, J$_2$=3 Hz); 7.40 (5H, m); 7.95 (1H, d, J=8 Hz).

M$^+$ (C$_{24}$H$_{24}$N$_5$O$_2$Cl) 465.1536.

DESCRIPTION 8

4,9-Dihydro-4,9-dioxo-5- and 6-nitro-1H-naphtho[2,3-d]-v-triazoles 4,9-Dihydro-4,9-dioxo-H-naphtho[2,3-d]-v-triazole (5.0 g, 25 mmole) was dissolved in sulphuric acid (30 ml) and fuming nitric acid (d=1.52, 30 ml) was added cautiously. The mixture was heated so that the internal temperature rose to 90°-100°. After 10 minutes at this temperature the mixture was poured onto ice (500 g), and the resulting precipitate filtered off, washed with water, and dried to yield a bright yellow powder (4.46 g, 74%). HPLC and NMR showed this to be a mixture of 5-nitro and 6-nitro derivatives in a ratio of ca 9:1 respectively.

Fractional recrystallisation from aqueous ethanol afforded pure 5-nitro compound of mp 213°-5°d (EtOH/H$_2$O), $v_{max}$ (mull) 3425 (br), 2600 (br), 1700, 1600, 1540, 1505 cm$^{-1}$.

δ[(CD$_3$)$_2$CO]: 6.5 (3H, br, exchangeable); 7.30 (1H, m); 7.80 (2H, m).

Found: C, 49.34; H, 1.71; N, 23.22. C$_{10}$H$_4$N$_4$O$_4$ requires C, 49.19; N, 1.65; N, 22.95%.

The 6-nitro compound was isolated from the enriched mother liquors by chromatography on silica, gradient eluting with ethyl acetate-methanol, mp 253°-4° (dec) (MeOH), $v_{max}$ (mull) 3225 (br), 1700, 1607, 1600, 1540 cm$^{-1}$.

δ[(CD$_3$)$_2$CO]: 6.5 (3H, br, exchangeable); 8.60 (1H, d, J=9 Hz); 8.85 (1H, dd, J$_1$=9, J$_2$=2 Hz); 9.00 (1H, d, J=2 Hz).

Found: C, 49.36; H, 1.57; N, 22.84. C$_{10}$H$_4$N$_4$O$_4$ requires C, 49.19, H, 1.65; N, 22.95%.

DESCRIPTION 9

4,9-Dihydro-4,9-dioxo-5-hydroxy-1H-naphtho[2,3-d]-v-triazole

A solution of the sodium salt of 4,9-dihydro-4,9-dioxo-5-nitro-1H-naphtho[2,3-d]-v-triazole (2.70 g, 10 mmole) in dimethyl sulphoxide (DMSO, 20 ml) was added to a solution of sodium acetaldoxime [from sodium hydride (80%, 1.0 g, 33 mmole) and acetaldoxime (1.80 g, 30 mmole)] in DMSO (35 ml). The mixture was stirred for 20 hours at ambient temperature and then poured into water (500 ml). The resulting solid was filtered off, washed with water, and dried to yield (1.67 g, (76.5%) of the title compound, mp (CHCl$_3$) 235° (dec) $v_{max}$(KBr) 3480, 2750 (br), 1695, 1655, 1645, 1600, 1575, 1510 cm$^{-1}$.

δ [(CD$_3$)$_2$CO]: 5.7 (4H, br, exchangeable); 7.33 (1H, M); 7.77 (2H, m).

λ$_{max}$ (EtOH) nm 219 (Em=19,700); 246 (23,300); 270 (10,800); 397 (4,900). Found: C, 55.82; H, 2.14; N, 19.33. C$_{10}$H$_5$N$_3$O$_3$ requires C, 55.82; H, 2.14; N, 19.53%.

Similarly, the mixed 5- and 6-nitro compounds were converted to a mixture of 4,9-dihydro-4,9-dioxo-5-hydroxy-1H-naphtho[2,3-d]-v-triazole and its 6-hydroxy isomer from which the 6-hydroxy compound was isolated. This was identical to the material isolated by photolysis of 4,9-dihydro-4,9-dioxo-1H-naphtho[2,3-d]-v-triazole.

DESCRIPTION 10

4,9-Dihydro-4,9-dioxo-5-hydroxy-N-(4-methoxybenzyl)-naphtho[2,3-d]-v-triazole 4,9-Dihydro-4,9-dioxo-5-hydroxy-1H-naphtho[2,3-d]-v-triazole (430 mg, 2 mmole) was stirred with potassium carbonate (152 mg, 1.1 mmole) and 4-methoxybenzyl chloride (329 mg, 2.10 mmole) in DMF (25 ml) at 50° for 22 hours. The DMF was evaporated in vacuo and the residue was partitioned between chloroform and dilute sodium hydroxide. Evaporation of the chloroform yielded 550 mg of a crude mixture of the three isomers of the title compound. These were identified by their tlc properties, the fastest running on silica being designated isomer A, the second being isomer B and the slowest being isomer C. Chromatography on silica eluting with chloroform-petroleum ether (4:1) gave all three isomers in reasonable purity. The total yield was 346 mg (51.6%).

Isomer A
m.p. 232°.
$\nu_{max}$ (CHCl$_3$) 2980 (br), 1695, 1655, 1625, 1525, 1515 cm$^{-1}$.
δ (DMSO) 3.73 (3H, s); 5.85 (2H, s); 7.18 (4H, AB quartet, J 8.5 Hz, Δν 45 Hz); 7.40 (1H, m); 7.75 (2H, m).
M+ ($C_{18}H_{13}N_3O_4$): 335.0907 Found C, 64.95; H, 3.55; N, 12.47.
$C_{18}H_{13}N_3O_4$ requires C, 64.47; H, 3.91; N, 12.53%.
$\lambda_{max}$ (EtOH) 229 (Em 10,200) 249 (9,400).

Isomer B
mpt 204° (EtOH/CHCl$_3$).
$\nu_{max}$ (mull) 1695, 1650, 1610, 1545, 1515 cm$^{-1}$.
δ (CDCl$_3$) 3.84 (3H, s);
5.92 (2H, s); 7.16 (4H, AB quartet, J 9 HZ, Δ ν 48 Hz); 7.80 (2H, m); 8.32 (1H, m), 11.86 (1H, s, exch.).
$\lambda_{max}$ (MeOH) 225, 245, 276 nm.

Isomer C
mpt 208° (EtOH/CHCl$_3$).
$\nu_{max}$ (mull) 1680, 1645, 1620, 1550, 1520 cm$^{-1}$.
M+ ($C_{18}H_{13}N_3O_4$) 335.0929.
δ (DMSO) 3.72 (3H, s); 5.93 (2H, s); 7.14 (4H, AB quartet J 9 Hz Δ, ν 38 Hz); 7.44 (1H, S); 7.76 (2H, m), 12.10 (1H, s, exch.).
Found C; 64.43; H, 4.07; N; 12.07. $C_{18}H_{13}N_3O_4$ requires C, 64.47; H, 3.91; N; 12.53%.
$\lambda_{max}$ (MeOH) 225, 247, 273 nm.

DESCRIPTION 11

5-{3-[4-(4-Chlorobenzyl)-1-piperazinyl]-propyloxy}-4,9-dihydro-4,9-dioxo-5-hydroxy-N-(4-methoxybenzyl)naphtho-[2,3-d]-v-triazole (a) 4,9-Dihydro- 4,9-dioxo-N-(4-methoxybenzyl)-naphtho-[2,3-d]-trizole (isomer C), (1.150 g, 3.43 mmole), triphenyl phosphine (1.380 g, 5.25 mmole) and 3-[4-(4-chlorobenzyl)-piperazin-1-yl]-propan-1-ol (0.920 g, 3.43 mmole) were dissolved in dry tetrahydrofuran (30 ml), and diethyl azodicarboxylate (0.904 g, 5.25 mmole) dissolved in THF (5 ml) was added with stirring at room temperature. After 5 minutes examination of the mixture by HPLC showed that reaction was essentially complete, after a further 0.5 hour reacton time the mixture was cooled in ice and dry hydrogen chloride was passed through the solution for 1 minute. A sticky yellow solid was precipitated, which was collected and recrystallised from ethanol to give 0.894 g of HPLC and TLC homogeneous material. A small sample was further recrystallised from ethanol to give material of m.p. 224°-5°.

$\nu_{max}$ (KBr) 3420, 2360, 1680, 1615, 1585, 1520 cm$^{-1}$;
δ (DMSO) 2.32 (2H, m); 3.50 (10H, m); 3.75 (3H, s); 4.38 (2H, s); 4.40 (2H, m) 5.92 (2H, s); 7.16 (4H, AB quartet, J 9.5 Hz, Δ ν 35 Hz); 7.64 (7H, m).
Found: C, 54.92; H, 5.33; N, 9.89; Cl, 15.77; $C_{32}H_{32}ClN_5O_4.2HCL.2H_2O$ requires: C, 55.29; H, 5.51; N, 10.08; Cl, 15.40%).

(b) Similar reactions using the A and B isomers gave the corresponding products, again isolated as their hydrochloride.

Isomer A mp 237°-40°.
$\nu_{max}$ (KBr) 3420, 2400, 1690, 1680, 1615, 1585, 1515 cm$^{-1}$.
(Found: Cl, 15.17; $C_{32}H_{32}ClN_5O_4.2HCL0.2H_2O$ requires: Cl, 15.40%).

Isomer B mp 208°.

EXAMPLE 4

5-{3-[4-(4-Chlorobenzyl)-1-piperazinyl]-propyloxy}-4,9-dihydro-4,9-dioxo-1H-naphtho-[2,3-d]-v-triazole

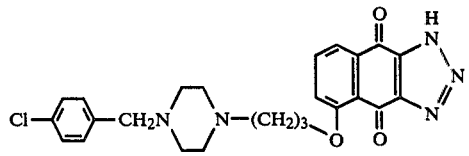

The product from isomer C above (0.750 g) was stirred with trifluoroacetic acid (30 ml) at 75°-80° C. for 1 hour after which time HPLC monitoring indicated complete deprotection. The reaction mixture was evaporated under reduced pressure, and the residue was extracted with hot ethanol. The filtered ethanol extract was evaporated under reduced pressure, and the residue was dissolved in 1M sodium hydroxide solution. Acidification to pH 5.0 with acetic acid, gave a yellow precipitate, which was collected, washed with water and dried to give (0.398 g) mp 197°-8°. This material was dissolved in chloroform and chromatographed on Kieselgel 60. The required product was eluted with chloroform-methanol (4:1), after the removal of less polar materials by elution with chloroform-methanol (9:1). Pure title compound had mp 207°.

ν (mull) 1645, 1580, 1275 cm$^{-1}$.
δ (DMSO) 2.16 (2H, m); 2.73 (2H, m); 3.33 (8H, m); 3.65 (2H, s); 4.23 (2H, t); 7.36 (4H, s); 7.53 (3H, m);
Three broad exchangeable protons occur between 2.0 and 4.0 δ.
M+($C_{24}H_{24}ClN_5O_3$)465.1544. (Found: C, 59.19; H, 5.04; N, 14.72; $C_{24}H_{24}ClN_5O_3.H_2O$ requires: C, 59.55; H, 5.41; N, 14.47%).

EXAMPLE 5

6-{3-[4-(4-Chlorobenzyl)-1-piperazinyl]propyloxy}-4,9-dihydro-4,9-dioxo-5-methyl-1H-naphtho[2,3-d]-v-triazole

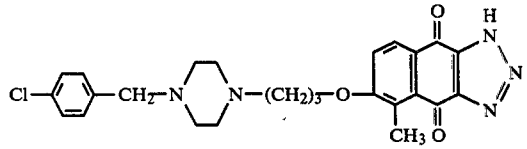

The title compound may be prepared in the manner described in Example 2.

EXAMPLE 6

6-{3-[4-(2-Chlorobenzyl)-1-piperazinyl]propyloxy}-4,9-dihydro-4,9-dioxo-5-methyl-1H-naphtho[2,3-d]-v-triazole

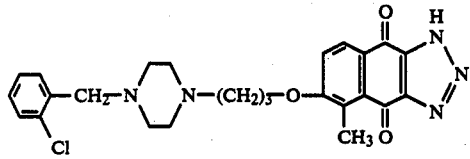

The title compound may be prepared in the manner described in Example 2.

PHARMACOLOGICAL DATA SECTION

Activities in biological test systems

The compounds were tested for their ability to:
(a) inhibit rat passive peritoneal anaphylaxis; and
(b) antagonise the spasmogenic effects of histamine on isolated guinea pig ileum.
The methods used are described below.
(a) Rat passive peritoneal anaphylaxis (PPA)
The method has been described previously (Ross, Janet W., Smith, H. and Spicer, Barbara A. Increased vascular permeability during passive peritoneal anaphylaxis in the rat, Int Arch Allergy appl Immun, 51, 226, 1976).

Animals

Charles River Sprague Dawley male rats of 225–275 g and Dunkin Hartley male white guinea pigs of 250–300 g were used.

Antiserum

This was raised in rats in one of two ways.

Method 1

Charles River Sprague Dawley male rats of 225 to 275 g were given subcutaneous injections of 10 μg of ovalbumin (chicken egg albumin; crystallised and lyophilised, grade 3, Sigma London), in 0.5 ml of a suspension prepared by adding 1 ml of a 0.1 mg/ml solution of ovalbumin, in isotonic saline, to 4 ml of a 1% suspension of aluminium hydroxide in saline (Alhydrogel; Miles Laboratories, England; diluted 1:1 with isotonic saline). The rats were bled on day 10.

Method 2

Charles River Sprague Dawley male rats of 225 to 300 g were given intraperitoneal injections of 0.5 ml of Bordetella pertussis vaccine ($4 \times 10^{10}$ organisms/ml Burroughs Wellcome, London) and subcutaneous injections of 0.5 ml of an emulsion of 100 mg of ovalbumin of 2 ml of isotonic saline and 3 ml of Freund's incomplete adjuvant (Pifco Laboratories, Michigan USA). The rats were bled on day 18.

Thereafter:

The rats were bled by cardiac puncture, the blood was pooled, from groups of rats treated similarly, and the serum separated, stored at $-20°$ and thawed only once before use. The serum sensitised rats for passive cutaneous anaphylaxis (carried out as described: Spicer, Barbara A; Ross, Janet W and Smith, H; Inhibition of immediate hypersensitivity reactions in the rat by disodium cromoglycate and a nitroindanedione, Clin exp, Immunol, 21, 419, 1975) to a dilution of 1:32 to 1:64 persisting for at least 72 hours after sensitisation.

Passive peritoneal anaphylaxis

Rats were given intraperitoneal injections of 2 ml of a 1:5 dilution of the rat anti-serum in isotonic saline. Two hours later 0.3 ml of a 5% solution of Pontamine Sky Blue (Raymond A. Lamb, London) in isotonic saline was injected intravenously, followed by an intraperitoneal injection of the test compound in 1 ml of saline; (control rats received 1 ml of saline); followed 30 seconds later by an intraperitoneal injection of 5 ml of a Tyrode solution containing 50 μg/ml heparin and 0.4 mg/ml of ovalbumin. The concentrations of the compounds were quoted as those in the 6 ml of fluid injected intraperitoneally. Exactly 5 minutes after challenge the rats were stunned and bled and their peritoneal fluids were collected by opening their peritoneal cavities over funnels into polycarbonate tubes in ice. The supernatants were separated from the cellular residue by centrifuging at 150 g for 5 minutes and any samples obviously contaminated with blood were discarded for estimattion of dye, histamine and SRS-A. Groups of at least 5 rats were used for each dose of compound and the treatments were randomised.

Assay of peritoneal fluids

Collected peritoneal fluids were immediately cooled to $0°$ C. and centrifuged and the supernatant fluids assayed for dye within 2 hours. 0.5 ml samples of the supernatants were added to 1 ml of 12% trichloracetic acid and stored at $-20°$ C. and used to assay for histamine. The remainders of the supernatant fluids were placed in a boiling water bath for 5 minutes and stored frozen at $-20°$ C. until assayed for SRS-A.

Dye Assay

The optical densities (OD) at 625 nm of the supernatants were determined. Samples were taken from supernatants with an OD greater than 2 and diluted in Tyrode's solution before reading.

Histamine Assay

Histamine was assayed using an automated spectrofluorimetric system (Technicon Autoanalyser) by a method similar to that of Evans, D.P., Lewis, J. A. and Thomson, D. S.; (An automated fluorimetric assay for the rapid determination of histamine in biological fluids. Life Sci 12,327, 1973). At the concentrations used the compounds tested did not interfere with the assay.

SRS-A Assay

SRS-A was assayed on the isolated guinea pig ileum preparation in the presence of atropine ($5 \times 10^{-7}$M) and mepyramine maleate ($10^{-6}$M), the latter to abolish the histamine response. (Brocklehurst, W. E., The release of histamine and formulation of a slow reacting substance (SRS-A) during anaphylactic shock. J Physiol Lond 151, 416, 1960). Bulked peritoneal fluids from passively sensitised and challenged rats were centrifuged, heated, stored at $-20°$ C. in 0.5 ml aliquots, and used as a reference SRS-A standard, and arbitrarily designated as containing 10 units per ml. Concentrations of the unknown were bracketed by reference SRS-A samaples. At the concentrations used, the compounds tested did not interfere with the assay.

(b) Anti-histamine activity

The anti-histamine activity of these compounds were measured in terms of $pA_2$ values on guinea pig ileum using the method described by Arunlakshana, O. and Schild, H. O. (Brit J Pharm, 14, 1959, 48).

The $pA_2$ is defined as the negative logarithm of the molar concentration of antagonist that will reduce the response of a double dose of agonist to that of a single dose.

Method

Assays were carried out using strips of terminal guinea pig ileum suspended in a 4 ml capacity organ bath. The ileum was immersed in aerated Tyrode solution at a temperature of 30° C. and a tension of 1 gm was applied to the gut. Longitudinal contractions of the gut were recorded isotonically using a 2LD01 Devices transducer, a R2502-2 Devices optical wedge and a RE511.20 Smiths servoscribe flat bed recorder.

The tissue was constantly immersed in Tyrode solution washing was by fluid displacement from below. Steady responses of the gut to histamine were obtained by adding histamine solutions in a volume of 0.1–0.2 ml to the bath.

Dose response curves were established for histamine using either a 3×3 or 4×4 Latin square design for the administration of the histamine doses.

The antagonists were then added to the Tyrode solution to give final concentrations ranging from 5 ng/ml to 640 ng/ml. The dose response curve to histamine were re-established in the presence of increasing doses of the antagonists.

Calculation of the $pA_2$ values

The height of the response was measured in mms and a mean value calculated. Parallel log dose/response curves were plotted on semi-log graph paper for histamine in the absence and presence of the antagonists. The dose of histamine which produced a response of 100 mms were obtained for each curve from the graph and the ratio designated CR was calculated from $$\frac{\text{dose of histamine to give response 100 mms in presence of antagonist}}{\text{dose of histamine to give response 100 mms in absence of antagonist}}$$

A further graph of log CR-1 against the negative log of the molar concentration of the antagonist in the Tyrode solution was then plotted. The $pA_2$ value was obtained where the line bisected the x-axis.

Results

The results obtained in these tests, which are shown in the following Table, demonstrate the ability of the compounds not only to inhibit the release of mediator substances but also to antagonise the effects of released histamine.

TABLE

| Compound | Conc$^n$ injected ip (M) | Concentration in peritoneal fluid as % of mean of controls. (Mean ± SEM, 5-7 rats per group) | | |
|---|---|---|---|---|
| | | Histamine | SRS-A | Dye |
| Example 1 | $2 \times 10^{-5}$ | 16 ± 2 | 75 ± 13 | 29 ± 2 |
| | $10^{-5}$ | 17 ± 3 | 39 ± 8 | 38 ± 3 |
| | $2 \times 10^{-6}$ | 23 ± 3 | 119 ± 25 | 47 ± 6 |
| | $10^{-6}$ | 27 ± 5 | 65 ± 18 | 54 ± 6 |
| | $10^{-7}$ | 90 ± 16 | 109 ± 18 | 75 ± 7 |
| Example 3 | | | | |
| Example 4 | $10^{-5}$ | 10 ± 1 | | 43 ± 2 |
| | $10^{-6}$ | 27 ± 4 | | 60 ± 11 |
| | $10^{-7}$ | 67 ± 8 | | 85 ± 9 |

Antihistamine activity (in vitro)

| Compound No | $pA_2$ values obtained in different assays |
|---|---|
| 1 | 9.0 9.3 8.9 9.3 |
| 3 | 9.1 9.0 |
| 4 | 6.05 6.1 7.2 6.5 |

Toxicity

No toxic effects were observed in these tests.

What we claim is:

1. A compound selected from the group consisting of a piperazine of the formula:

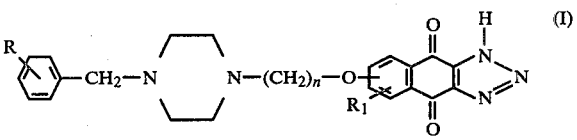

and the pharmaceutically acceptable salts thereof wherein

R is hydrogen, halo, alkyl of 1 to 4 carbon atoms or alkoxy of 1 to 4 carbon atoms;

$R_1$ is hydrogen or alkyl of 1 to 6 carbon atoms; and n is 1 to 6.

2. A compound according to claim 1 wherein R is halo in the 2-, 3- or 4-position of the depicted phenyl ring.

3. A compound according to claim 1 wherein the 4-benzylpiperazinyl-alkoxy side chain is in the 5- or 6-position of the depicted napthotriazole system.

4. A compound according to claim 1, wherein $R_1$ is alkyl of 1 to 6 carbon atoms.

5. A compound according to claim 1 wherein n is 2, 3 or 4.

6. A compound according to claim 1 wherein said piperazine is of the formula:

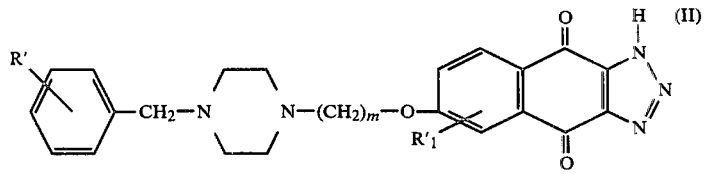

wherein

R' is hydrogen or halo,
R₁' is hydrogen or alkyl of 1 to 6 carbon atoms, and m is 2, 3 or 4.

7. A compound according to claim 6 wherein R' is chloro in the 2-, 3- or 4-position of the depicted phenyl ring.

8. A compound according to claim 6 wherein R₁' is hydrogen or methyl.

9. A compound according to claim 6 wherein m is 3.

10. 6-{3-[4-(4-Chlorobenzyl)-1-piperazinyl]propyloxy}-4,9-dihydro-4,9-dioxo-1H-naphtho[2,3-d]-v-triazole, or a pharmaceutically acceptable salt thereof.

11. 5-{3-[4-(4-1-piperazinyl]propyloxy}-4,9-dihydro-4,9-dioxo-1H-naphtho[2,3-d]-v-triazole, or a pharmaceutically acceptable salt thereof; or
6-{3-[4-(2-Chlorobenzyl)-1-piperazinyl]propyloxy}-4,9-dihydro-4,9-dioxo-1H naphtho [2,3-d]-v-triazole, or a pharmaceutically acceptable salt thereof; or
6-{3-[4-(4-Chlorobenzyl)-1-piperazinyl]propyloxy}-4,9-dihydro-4,9-dioxo-1H-naphtho[2,3-d]-v-triazole, or a pharmaceutically acceptable salt thereof, or
6-{3-[4-(2-Chlorobenzyl)-1-piperazinyl]propyloxy}-4,9-dihydro-4,9-dioxo-5-methyl-1H-naphtho[2,3-d]-v-triazole, or a pharmaceutically acceptable salt thereof.

12. A pharmaceutical composition comprising an antiallergenically effective amount of a compound according to claim 1 in combination with a pharmaceutically acceptable carrier.

13. A compound of formula

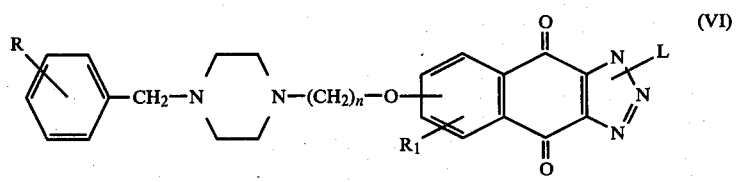

wherein
R, R₁ and n are as in claim 1, and
L is a labile benzyl group or trityl.

14. The method of treating an allergic response in a human which comprises administering thereto the pharmaceutical composition of claim 12.

15. A compound according to claim 13, wherein L is benzyl substituted in the phenyl moiety by one, two or three alkoxy of 1 to 4 carbon atoms, or is trityl.

* * * * *